United States Patent
Wall (10) Patent No.: US 10,420,593 B2
(45) Date of Patent: Sep. 24, 2019

(54) SPINAL CORRECTION SYSTEM AND METHOD

(71) Applicant: Warsaw Orthopedic, Inc, Warsaw, IN (US)

(72) Inventor: Daniel Paxton Wall, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 159 days.

(21) Appl. No.: 15/216,454

(22) Filed: Jul. 21, 2016

(65) Prior Publication Data

US 2018/0021070 A1    Jan. 25, 2018

(51) Int. Cl.
    *A61B 17/70* (2006.01)

(52) U.S. Cl.
    CPC ...... *A61B 17/7091* (2013.01); *A61B 17/7002* (2013.01); *A61B 17/7035* (2013.01); *A61B 17/7079* (2013.01)

(58) Field of Classification Search
    CPC ............ A61B 17/7077; A61B 17/7079; A61B 17/708
    See application file for complete search history.

(56) References Cited

U.S. PATENT DOCUMENTS

| | | | |
|---|---|---|---|
| 6,126,660 A * | 10/2000 | Dietz | A61B 17/025 606/90 |
| 7,951,175 B2 * | 5/2011 | Chao | A61B 17/7077 606/279 |
| 7,981,115 B2 | 7/2011 | Justis | |
| 8,372,081 B1 * | 2/2013 | Schafer | A61B 17/7077 606/105 |
| 8,951,257 B2 | 2/2015 | Lenke | |
| 2006/0095035 A1 | 5/2006 | Jones et al. | |
| 2006/0149278 A1 * | 7/2006 | Abdou | A61B 17/7077 606/90 |
| 2007/0173831 A1 | 7/2007 | Abdou | |
| 2010/0030283 A1 * | 2/2010 | King | A61B 17/7037 606/86 A |
| 2010/0036443 A1 * | 2/2010 | Hutton | A61B 17/7032 606/86 R |
| 2011/0130793 A1 * | 6/2011 | Woolley | A61B 17/0206 606/279 |
| 2011/0172714 A1 * | 7/2011 | Boachie-Adjei | A61B 17/708 606/264 |
| 2013/0184763 A1 | 7/2013 | McClintock et al. | |
| 2015/0066088 A1 * | 3/2015 | Brinkman | A61B 17/7077 606/264 |
| 2016/0262810 A1 * | 9/2016 | Meyer | A61B 17/7076 |

OTHER PUBLICATIONS

International Search Report and Written Opinion of the International Searching Authority, European Patent Office, PCT/US2017/042976, dated Nov. 2, 2017.

* cited by examiner

*Primary Examiner* — Julianna N Harvey (57) ABSTRACT

A surgical instrument comprises a fulcrum including a first surface that defines a cavity configured for disposal of a first implant support. A second surface is movable relative to the fulcrum and engageable with the support to fix the first surface with the support. A third surface is connected with the second surface such that the second surface is translatable relative to the support and the third surface is engageable with a second implant support. In some embodiments, spinal constructs, implants, systems and methods are disclosed.

20 Claims, 8 Drawing Sheets

SPINAL CORRECTION SYSTEM AND METHOD

TECHNICAL FIELD

The present disclosure generally relates to medical devices for the treatment of spinal disorders, and more particularly to a surgical system and method for correction of a spinal disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, corpectomy, discectomy, laminectomy, fusion, fixation and implantable prosthetics. Correction treatments used for positioning and alignment of vertebrae may employ implants, such as, for example, spinal constructs and interbody devices, for stabilization of a treated section of a spine. In some cases, the spinal constructs may be manipulated with surgical instruments for compression and distraction of vertebrae. This disclosure describes an improvement over these prior technologies.

SUMMARY

In one embodiment, a surgical instrument is provided. The surgical instrument comprises a fulcrum including a first surface that defines a cavity configured for disposal of a first implant support. A second surface is movable relative to the fulcrum and engageable with the support to fix the first surface with the support. A third surface is connected with the second surface such that the second surface is translatable relative to the support and the third surface is engageable with a second implant support. In some embodiments, spinal constructs, implants, systems and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system comprises one or more surgical instruments that can be employed with a spinal construct for treating a spine disorder. In some embodiments, the present surgical system can be employed with a pedicle subtraction osteotomy and a posterior vertebral column resection to correct angular and fixed kyphotic deformity, such as post traumatic deformity, congenital deformity and/or post infectious deformity.

In some embodiments, the present surgical system comprises a surgical instrument including an adjustable compression and/or distraction fulcrum. In some embodiments, the present surgical system comprises a surgical instrument including an adjustable fulcrum that can be used in conjunction with multi-axial screws (MAS), reinforcement sleeves and/or compressor/distractor pliers to distract or compress an intervertebral disc space.

In some embodiments, the present surgical system comprises a surgical instrument including a fulcrum having an arm. In some embodiments, the present surgical system comprises a surgical instrument including a body engageable with the fulcrum arm. In some embodiments, the present surgical system comprises a surgical instrument including a lock, such as, for example, a clamp screw. In some embodiments, the clamp screw is actuated to translate the fulcrum arm to intersect an inner diameter of the body. In some embodiments, the fulcrum arm and the body are configured to clamp a screw extender in a locked orientation. In some embodiments, the fulcrum arm includes a stop element, such as, for example, a pin configured to resist and/or prevent the fulcrum from disengaging from the body.

In some embodiments, the lock includes a pressure plate. In some embodiments, the lock includes a clamp plate. In some embodiments, the lock includes a plate stop. In some embodiments, when the clamp screw is in a first orientation, the fulcrum arm can translate relative to the body. In some embodiments, the pressure plate is spring loaded to apply a force to the fulcrum arm to provisionally fix the fulcrum with the screw extender. In some embodiments, the fulcrum arm is configured to apply a force to an outer diameter of the screw extender as the fulcrum is translated for positioning to provisionally fix the fulcrum with the screw extender.

In some embodiments, the lock is configured such that the plate stop is pressed onto an end of a clamp screw shaft and welded thereto. In some embodiments, this configuration facilitates fixation of the components of the lock by trapping the clamp plate that in turn traps the pressure plate. In some embodiments, the fulcrum arm is attached after the plate stop is welded. In some embodiments, the stop pin is then assembled with the fulcrum arm.

In some embodiments, the pressure plate includes tabs to facilitate fixation of the lock components. In some embodiments, the clamp plate includes slots configured for disposal of the tabs to capture the pressure plate to resist and/or prevent disassembly of the component parts.

In some embodiments, the present surgical system is employed with a method that includes the step of actuating the fulcrum to allow the fulcrum to slide up and down an extender sleeve and to adjust the width of the fulcrum. In some embodiments, a spring loaded pressure plate facilitates provisional fixation of the fulcrum with a screw extender. In some embodiments, the method includes the step of releasing the fulcrum to lock the fulcrum in a selected position with one or more extenders. In some embodiments, the method includes the step of squeezing pliers below a selected position of the fulcrum to compress vertebrae. In some embodiments, the method includes the step of squeezing pliers above a selected position of the fulcrum to distract vertebrae.

In some embodiments, the surgical instrument includes a fulcrum style compressor that utilizes a fulcrum and a separate set of compression pliers. In some embodiments, the surgical instrument includes a fulcrum and pliers that are attached to screw extenders and actuated to either compress or distract vertebrae. In some embodiments, the surgical instrument includes a fulcrum that can be placed at multiple locations on screw extenders. In some embodiments, the present surgical system is employed with a method such that the pliers are drawn together, compressed and/or squeezed above the fulcrum and the disc space is distracted. In some embodiments, the present surgical system is employed with a method such that the pliers are drawn together, compressed and/or squeezed below the fulcrum and the disc space is compressed.

In some embodiments, the present surgical system is employed with a method that can compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, ankylosing spondylitis. In some embodiments, the present surgical system is employed to treat hyper-kyphosis, flat lumbar back and cervical hyper lordosis, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, lateral, postero-lateral, and/or anger-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made to the exemplary embodiments of the present disclosure, which are illustrated in the accompanying figures. Turning to FIGS. 1-6, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKEL-ITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal correction system 10 are configured for engagement with instrumentation and/or spinal constructs attached with vertebrae to manipulate tissue and/or correct a spinal disorder, such as, for example, a sagittal deformity, as described herein. In some embodiments, spinal correction system 10 may be employed with surgical procedures, such as, for example, corpectomy, discectomy and/or fracture/trauma treatment and may include fusion and/or fixation that employ implants to restore the mechanical support function of vertebrae.

Spinal correction system 10 includes a surgical instrument, such as, for example, a fulcrum 12. Fulcrum 12 includes a body 14 that defines an axis X1. Body 14 includes a surface 16 and a surface 18, and defines an interior cavity therebetween for disposal of one or more of the components of fulcrum 12. Body 14 extends between an end 20 and an end 22. In some embodiments, body 14 may include alternate configurations, such as, for example, arcuate, offset, staggered and/or angled portions. In some embodiments, surface 16 and/or surface 18 may include ridges to facilitate gripping of fulcrum 12, for example, to manipulate body 14, as described herein.

Body 14 includes an inner surface 30 that defines spaced apart openings 32, 32a with the interior cavity of body 14 disposed therebetween. Openings 32, 32a are configured for disposal and/or translation of an implant support, such as, for example, an extender 200, relative to fulcrum 12, as described herein. Openings 32, 32a each include a circular configuration. In some embodiments, the cross-section geometry of opening 32 and/or opening 32a may have alternate configurations, such as, for example, oval, oblong, triangular, polygonal having planar or arcuate side portions, irregular, uniform, non-uniform, consistent or variable. Body 14 defines a window 33 disposed between openings 32, 32a that provides access to the interior cavity of body 14 and/or an implant support disposed therein.

Body 14 includes a surface 40 that defines a passageway 42. Passageway 42 extends between ends 20, 22 and is oriented in parallel alignment with axis X1. Passageway 42 is configured for disposal of an arm, such as, for example, a slide 44, as described herein. In some embodiments, the cross-section geometry of passageway 42 may have various configurations, such as, for example, round, oval, oblong, triangular, polygonal having planar or arcuate side portions, irregular, uniform, non-uniform, consistent, variable, horseshoe shape, U-shape or kidney bean shape.

Slide 44 extends between an end 50 and an end 52. Slide 44 includes a leg 54 extending between ends 50, 52. Leg 54 is disposed with passageway 42 and oriented in parallel alignment with axis X1. Leg 54 includes a surface 56 oriented to face openings 32, 32a. Slide 44 is disposed with passageway 42 and oriented for engagement with a part, such as, for example, a pressure plate 46 disposed with the interior cavity of body 14.

Leg 54 includes a surface 70 that includes a plurality of teeth disposed in a linear configuration and defining a toothed rack 72. Pressure plate 46 is engageable with rack 72 in a non-locking orientation and a locking orientation of fulcrum 12. A lock 80 is engageable with rack 72 in the locking orientation, as described herein. In the non-locking orientation, lock 80 draws or backs out clamp plate 100 apart from slide 44 such that clamp plate 100 disengages from rack 72 and slide 44 can selectively translate relative to body 14, as described herein. In the non-locking orientation, pressure plate 46 is biased to engage and/or provisionally hold rack 72 with a force applied to slide 44 to maintain position of slide 44 and/or an implant support disposed with openings 32, 32a relative to body 14, as described herein. In the non-locking orientation, slide 44 and/or an implant support disposed with openings 32, 32a is selectively translatable relative to body 14 under the force from pressure plate 46. In the locking orientation, components of lock 80 are disposed in fixed engagement with rack 72 to resist and/or prevent translation of slide 44 and/or an implant support disposed with openings 32, 32a relative to body 14, as described herein. In some embodiments, one or more components of lock 80 are moveable into and out of engagement with rack 72 to facilitate translation of slide 44 relative to body 14 along axis X1 to increase and/or decrease a width w (FIG. 4) of fulcrum 12 for engaging and disengaging an implant support, such as, for example, extender 202, as described herein.

Pressure plate 46 includes a surface configuration that facilitates engagement and support of slide 44 with a wall 60 of body 14. Pressure plate 46 includes a surface 62 that defines an opening 64. Opening 64 is configured for disposal of one or more components of lock 80, as described herein.

Lock 80 is actuated by a screw 90. Screw 90 includes a handle 92 configured to facilitate manipulation of lock 80 between a non-locking orientation and a locking orientation, and/or translation of clamp plate 100 into and out of engagement with rack 72. Screw 90 includes a shaft 94 having a threaded surface 96. Surface 96 is engageable with clamp plate 100, which is configured for disposal with opening 64.

Clamp plate 100 includes a surface 102 having a plurality of teeth 104. Teeth 104 are configured for mating engagement with rack 72 to fix position of slide 44 with body 14 in a locking orientation. Clamp plate 100 includes a surface 108 that defines an opening 110. Opening 110 is configured for disposal of a plate stop 112. Plate stop 112 is configured retain clamp plate 100 with screw 90. In some embodiments, plate stop 112 is pressed onto a distal end of screw 90 and welded thereto. In some embodiments, this configuration of plate stop 112 with screw 90 maintains the assembly of the components of lock 80, slide 44 and body 14 by capturing clamp plate 100 and pressure plate 46, as described herein.

Surface 62 includes tabs 66 extending into opening 64. Clamp plate 100 is attached with screw 90 such that tabs 66 extend over clamp plate 100 to connect screw 90 with pressure plate 46. Tabs 66 are configured to resist and/or prevent disengagement of the components of lock 80 with plate stop 112.

Translation of screw 90 relative to body 14 causes clamp plate 100 to translate into and out of engagement with slide 44. Screw 90 is rotated in a counter-clockwise direction and translates, in a direction shown by arrow A in FIG. 4, to a non-locking orientation of lock 80 with slide 44. Screw 90 is connected with pressure plate 46. In some embodiments, screw 90 is connected with pressure plate 46 to prevent accidental disengagement when slide 44 is not assembled. Clamp plate 100 disengages rack 72 and slide 44 can selectively translate relative to body 14, in the direction shown by arrows C in FIG. 4 and as described herein.

Figure 1:
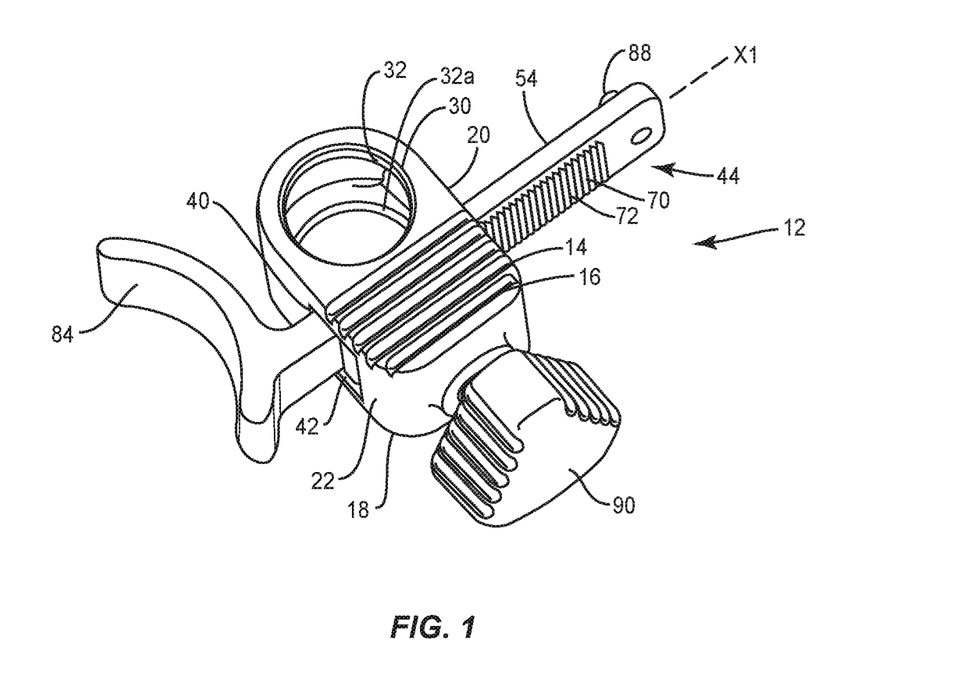
FIG. 1 is a perspective view of components of one embodiment of a surgical system in accordance with the principles of the present disclosure.
Figure 2:
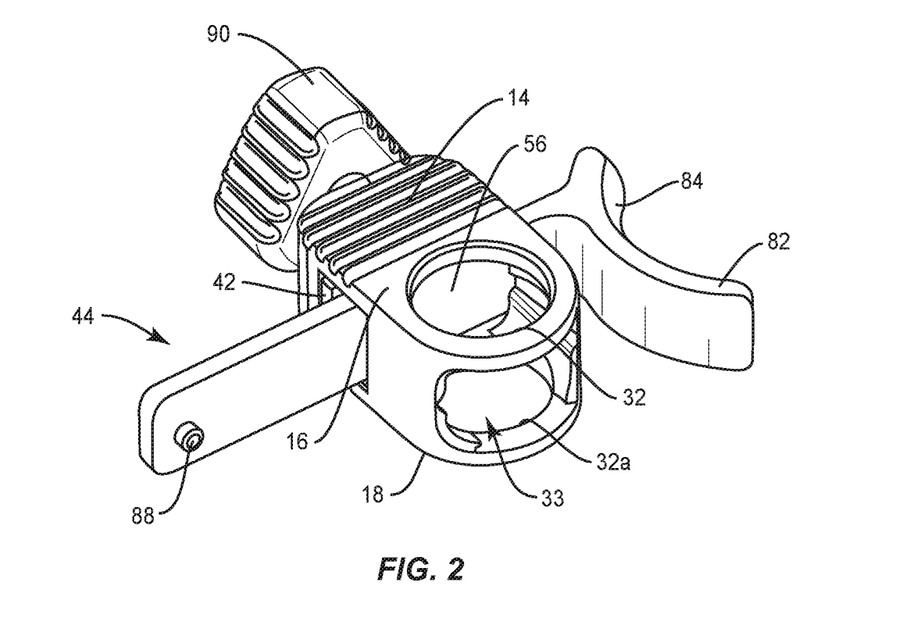
FIG. 2 is a perspective view of the components shown in FIG. 1.
Figure 3:
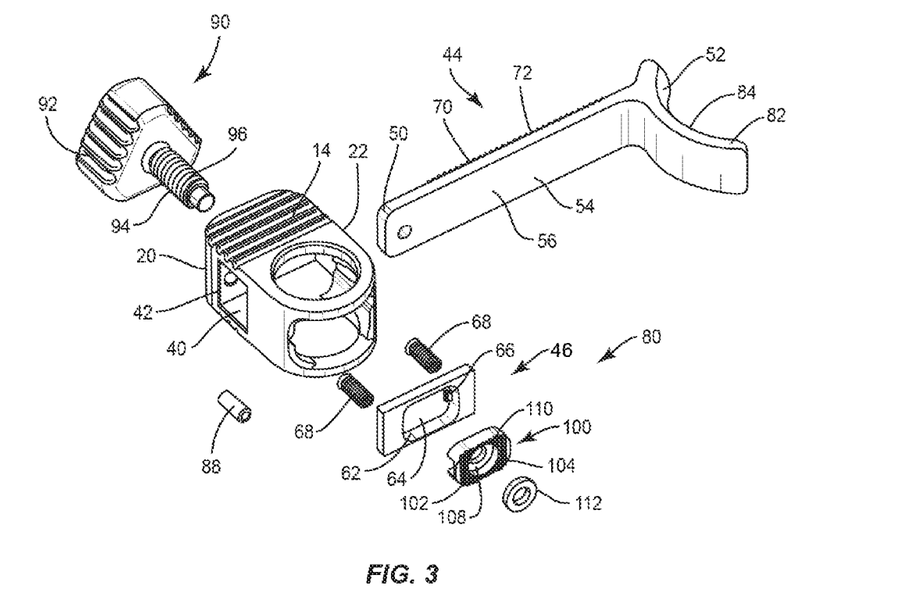
FIG. 3 is a perspective view of the components shown in FIG. 1 with parts separated.
Figure 4:
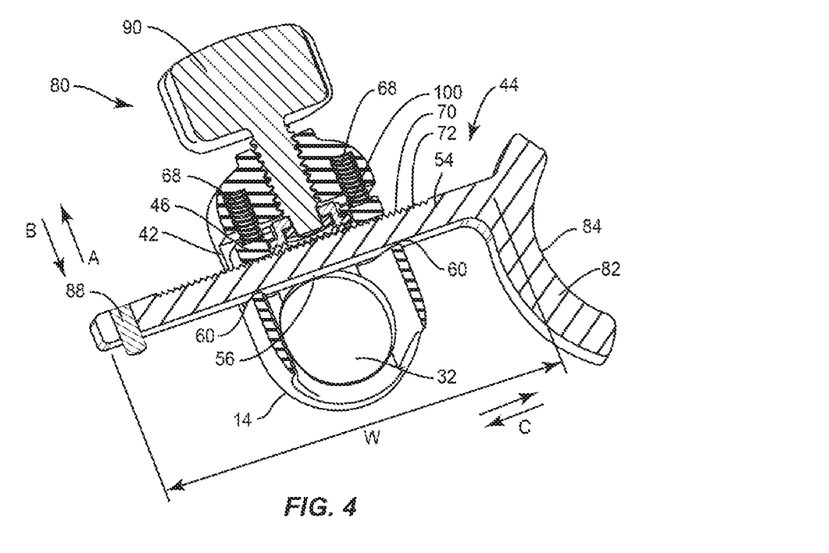
FIG. 4 is a cross section view of the components shown in FIG. 1.
Figure 5:
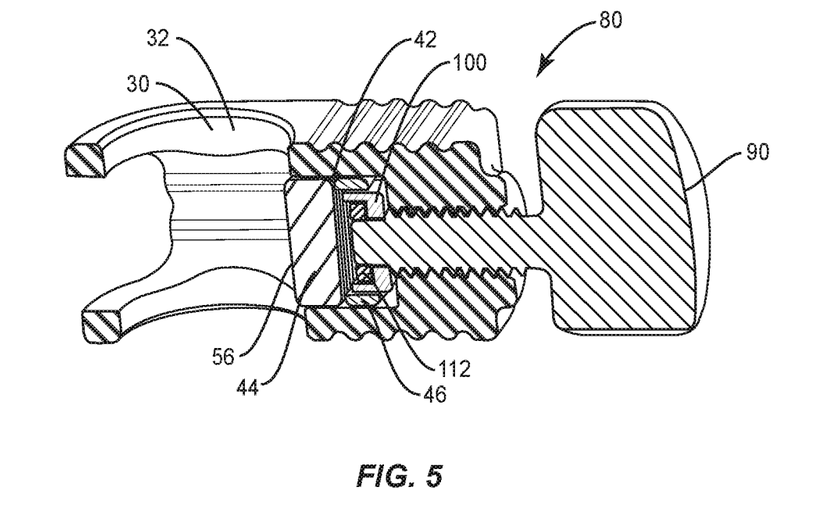
FIG. 5 is a cross section view of components of the system shown in FIG. 1.
Figure 6:
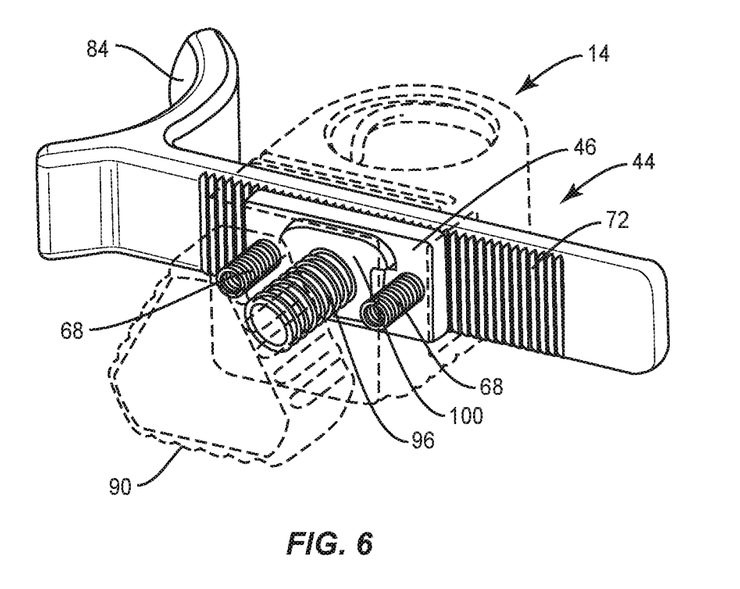
FIG. 6 is a perspective view, in part phantom, of the components shown in FIG. 1.

Springs 68 bias pressure plate 46, in a direction shown by arrow B in FIG. 4. In the non-locking orientation of lock 80 with slide 44, pressure plate 46 is biased to engage and/or provisionally maintain fixation with rack 72 with a force applied to slide 44 to maintain position of slide 44 relative to body 14. The force applied causes surface 56 to engage an implant support disposed with openings 32, 32a. In some embodiments, this configuration maintains position of slide 44 and/or an implant support with body 14 and applies pressure on an outside surface of the implant support when adjusting and/or sliding body 14 therealong.

Screw 90 is rotated in a clockwise direction and translates, in the direction shown by arrow B in FIG. 4, relative to body 14 causing clamp plate 100 to engage slide 44 and teeth 104 to engage rack 72 to fix position of slide 44 with body 14 in a locking orientation. In the locking orientation, lock 80 is disposed in fixed engagement with rack 72 to resist and/or prevent translation of slide 44 and/or an implant support relative to body 14, as described herein.

End 52 includes an end member 82 having a surface 84 configured for engagement with an implant support. In some embodiments, surface 84 includes a concave configuration to facilitate engagement with a surface of an implant support to fix position of fulcrum 12 with the implant support. Slide 44 is translatable relative to body 14 within passageway 42 to orient surface 84 with an implant support. In a non-locking orientation of lock 80 and slide 44, slide 44 is selectively translatable within passageway 42 relative to body 14. Surface 84 is moveable relative to body 14 for positioning with the implant support. In some embodiments, surface 84 is engaged with the surface of the implant support in a friction fit engagement. In some embodiments, end 50 includes a stopping element, such as, for example, a stop pin 88. Pin 88 is configured to resist and/or prevent slide 44 from disengaging from body 14 during translation of slide 44.

In operation, for example, screw 90 is rotated in a counter-clockwise direction and translates, in a direction shown by arrow A in FIG. 4, to a non-locking orientation of lock 80 with slide 44 such that plate stop 112 backs clamp plate 100 out from slide 44, as described herein. Fulcrum 12 is translatable relative to and along an outer surface of extender 200, in the directions shown by arrows D shown in FIG. 7, for selective positioning of fulcrum 12 with extender 200. Fulcrum 12 is movable along extender 200 for selective positioning therewith in connection with a surgical procedure, as described herein.

Clamp plate 100 is disengaged from rack 72 to allow translation of leg 54 in opposing axial directions within passageway 42 for selective positioning of surface 84 with extender 202. Slide 44 selectively translates relative to body 14, in the direction shown by arrows C in FIG. 4, to selectively adjust width w of fulcrum 12 to facilitate engagement with extender 202.

Upon selective positioning of fulcrum 12 with extenders 200, 202, springs 68 bias pressure plate 46 in the non-locking orientation of lock 80 with slide 44 to provisionally hold rack 72 to maintain position of slide 44 and extenders 200, 202 relative to body 14.

Figure 7:
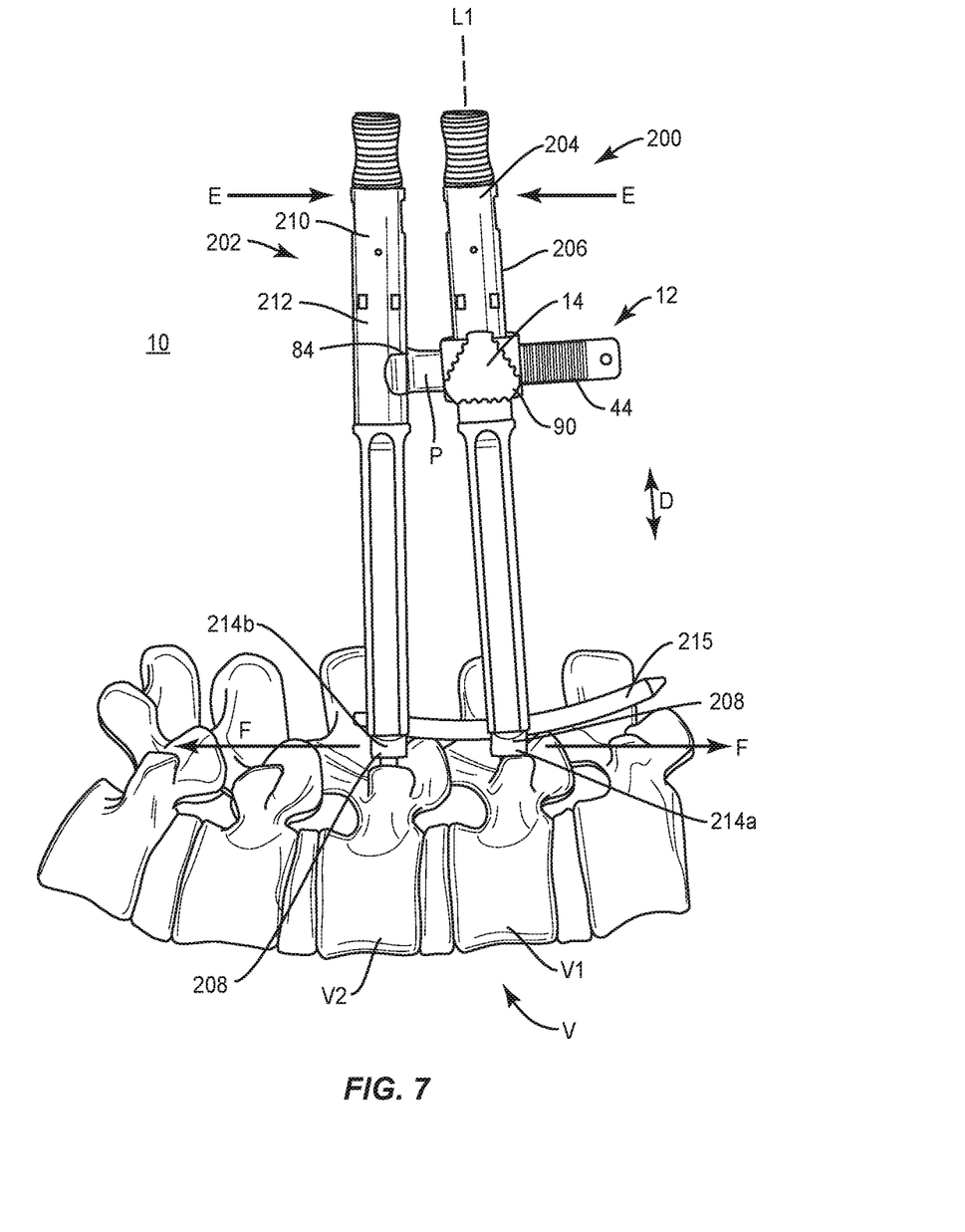
FIG. 7 is a perspective view of components of one embodiment of a surgical system in accordance with the principles of the present disclosure disposed with vertebrae.

Screw 90 is rotated in a clockwise direction and translates, in the direction shown by arrow B in FIG. 4, relative to body 14 causing teeth 104 to engage rack 72 to fix position of slide 44 with body 14 in a locking orientation of lock 80 with slide 44. In the locking orientation, lock 80 is disposed in fixed engagement with rack 72 to resist and/or prevent translation of slide 44 relative to body 14, and/or to fix position of fulcrum 12 with extenders 200, 202. In some embodiments, as shown in FIG. 7, fulcrum 12 is disposed with extender 200 to provide a pivot point P for extenders 200, 202 and apply a compression force, as shown by arrows E, to facilitate distraction of vertebrae V, as shown by arrows F. In some embodiments, as shown in FIG. 8, fulcrum 12 is disposed with extender 200 to provide a pivot point P for extenders 200, 202 and apply a compression force, as shown by arrows G, to facilitate compression of vertebrae V, as shown by arrows H.

In some embodiments, extender 200 includes a member, such as, for example, a sleeve 204. In some embodiments, sleeve 204 is configured as a reinforcement sleeve for connection with one or more spinal implants and/or constructs, surgical instruments and/or implant supports. Sleeve 204 extends along a longitudinal axis L1 and includes a surface 206. Surface 206 is configured for engagement with surface 30 of fulcrum 12 to facilitate manipulation of extender 200, as described herein. Sleeve 204 is configured for translation over a portion of a spinal construct 208, as shown in FIGS. 7-10. Sleeve 204 provides a reinforcement sleeve engageable with spinal construct 208 to resist and/or prevent relative movement therebetween. In some embodiments, sleeve 204 provides a reinforcement sleeve engageable with spinal construct 208 for treating spinal trauma and/or deformity disorders with a minimally invasive surgical technique. In some embodiments, sleeve 204 provides a reinforcement sleeve engageable with spinal construct 208 for employment with a trauma rack and/or small deformity maneuvers, as described herein. In some embodiments, sleeve 204 provides a reinforcement sleeve engageable with spinal construct 208 for manipulation of vertebrae during a surgical treatment, for example, to displace, pull, twist or align vertebrae.

Extender 202, similar to extender 200, includes a member, such as, for example, a sleeve 210. Sleeve 210 extends along a longitudinal axis L2 and includes a surface 212. Surface 212 is configured for engagement with surface 84 of fulcrum 12 to facilitate manipulation of extender 202, as described herein. Sleeve 210 is configured for translation over a portion of spinal construct 208, as shown in FIGS. 7-10, similar to extender 200.

Figure 8:
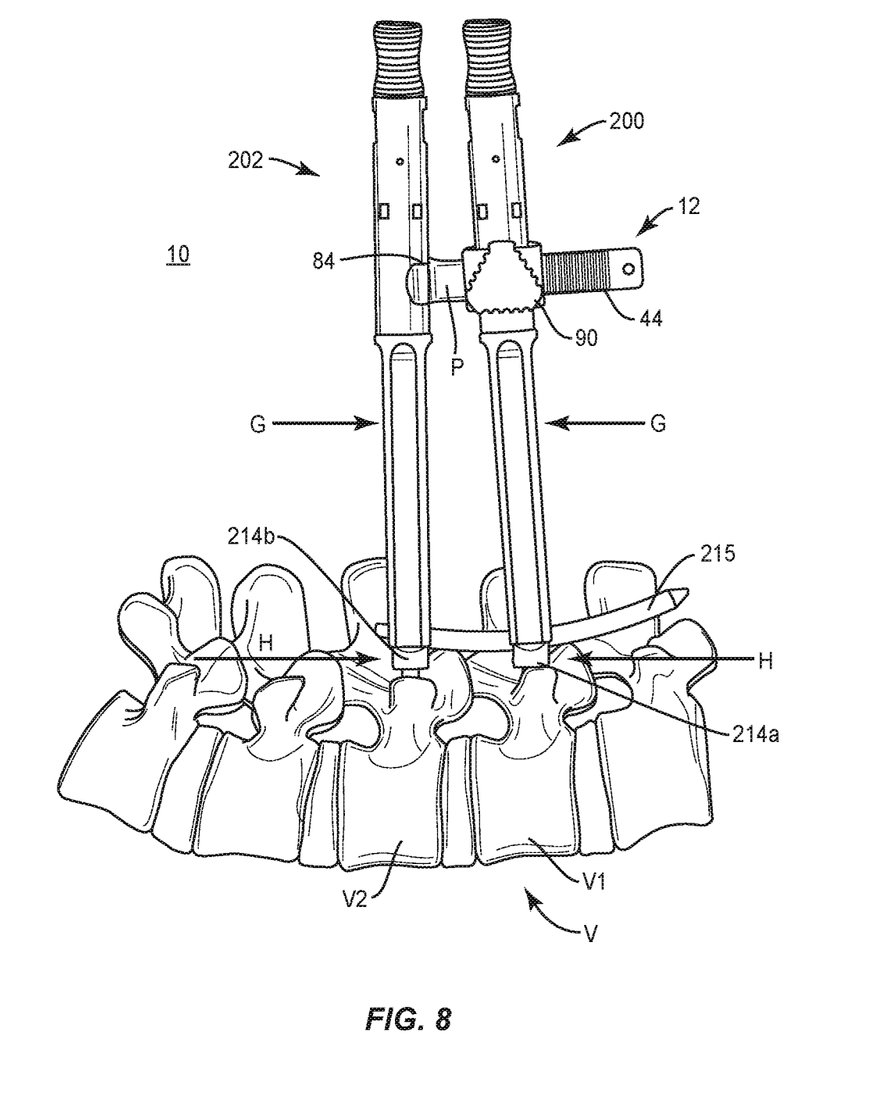
FIG. 8 is a perspective view of components of one embodiment of a surgical system in accordance with the principles of the present disclosure disposed with vertebrae.
Figure 9:
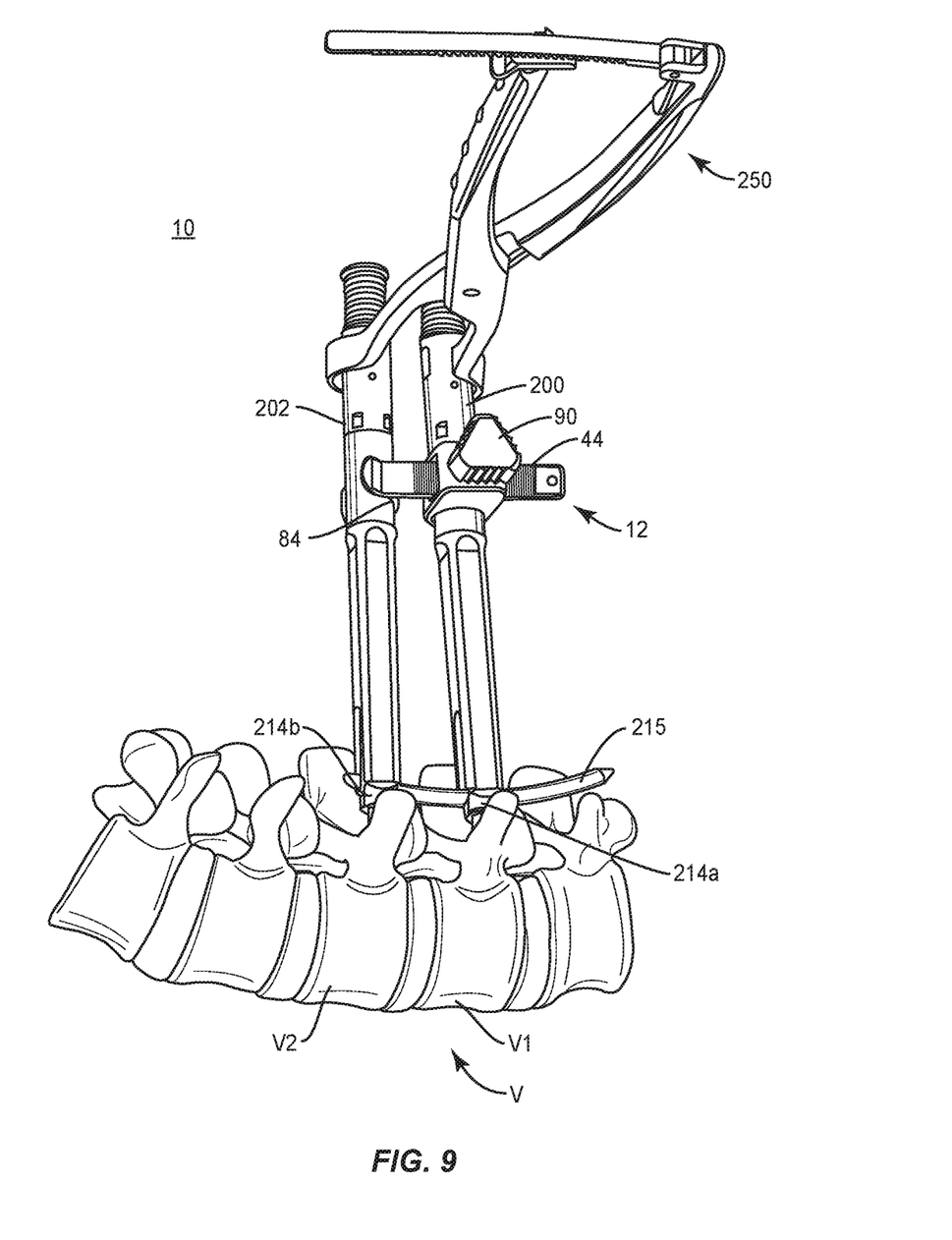
FIG. 9 is a perspective view of components of one embodiment of a surgical system in accordance with the principles of the present disclosure disposed with vertebrae.

In assembly, operation and use, spinal correction system 10 including fulcrum 12, similar to the systems and methods described with regard to FIGS. 1-6, is employed with a surgical procedure for treatment of a spine of a patient including vertebrae V, as shown in FIGS. 7-9. For example, spinal correction system 10 can be employed with a surgical correction treatment of an applicable condition or injury of an affected section of a spinal column and adjacent areas within a body, such as, for example, vertebral levels V1, V2 of vertebrae V. In some embodiments, spinal correction system 10 may be employed with one or a plurality of vertebra.

In use, to treat the affected section of vertebrae V, a medical practitioner obtains access to a surgical site including vertebrae V in any appropriate manner, such as through incision and retraction of tissues. In some embodiments, spinal correction system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. An incision is made in the body of the patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Pilot holes or the like are made in selected vertebra V1 and V2 for receiving bone fasteners 214a, 214b of spinal construct 208. A driver (not shown) is disposed adjacent vertebrae V at a surgical site and is manipulated to drive, torque, insert or otherwise connect bone fasteners 214a, 214b with vertebrae V1 and V2. A spinal rod 215 is connected with bone fasteners 214a, 214b. Extenders 200, 202 are delivered to the surgical site adjacent vertebrae V and oriented for manipulation, alignment and capture of spinal construct 208. For example, extender 200 is disposed with bone fastener 214a and an adjacent portion of spinal rod 215 and extender 202 is disposed with bone fastener 214b and an adjacent portion of spinal rod 215.

Fulcrum 12 is disposed adjacent extenders 200, 202. In a non-locking orientation, as described herein, clamp plate 100 is backed out from slide 44 and fulcrum 12 is translatable relative to and along an outer surface of extender 200, in the directions shown by arrows D shown in FIG. 7, for selective positioning of fulcrum 12 with extender 200. Slide 44 selectively translates relative to body 14, in the direction shown by arrows C in FIG. 4, to selectively adjust width w of fulcrum 12 to facilitate engagement with extender 202.

Upon selective positioning of fulcrum 12 with extenders 200, 202, in the non-locking orientation, as described herein, springs 68 bias pressure plate 46 to engage slide 44 and provisionally maintain position of slide 44 and extenders 200, 202 relative to body 14. Screw 90 is rotated in a clockwise direction and translates, in the direction shown by arrow B in FIG. 4, relative to body 14 causing teeth 104 to engage rack 72 to fix position of slide 44 with body 14 in a locking orientation of lock 80 with slide 44. In a locking orientation, lock 80 is disposed in fixed engagement with rack 72 to resist and/or prevent translation of slide 44 relative to body 14, and/or to fix position of fulcrum 12 with extenders 200, 202.

Surface 84 is engaged with surface 212 to facilitate compression and/or distraction of vertebrae V. As such, fulcrum 12 is releasably fixed with extenders 200, 202 to facilitate compression and/or distraction of vertebrae V. A surgical instrument, such as, for example, pliers 250 are engaged with extenders 200, 202, as shown in FIG. 9. Pliers 250 are connected with extenders 200, 202, which are engaged with spinal construct 208, in a configuration to rotate vertebrae V1, V2 about fulcrum 12, for example, in a compression and/or distraction treatment of vertebrae V.

Positioning of pliers 250 below fulcrum 12 compresses vertebrae V about fulcrum 12. In some embodiments, as shown in FIG. 8, fulcrum 12 is disposed with extender 200 to provide a pivot point P for extenders 200, 202 and apply a compression force, as shown by arrows G, to facilitate compression of vertebrae V, as shown by arrows H. Positioning of pliers 250 above fulcrum 12 distracts vertebrae V about fulcrum 12. In some embodiments, as shown in FIG. 7, fulcrum 12 is disposed with extender 200 to provide a pivot point P for extenders 200, 202 and apply a compression force, as shown by arrows E, to facilitate distraction of vertebrae V, as shown by arrows F. In some embodiments, pliers 250 are engaged with extenders 200, 202 to rotate vertebrae V1, V2 about fulcrum 12 for manipulating vertebrae V during a surgical correction treatment to derotate, displace, pull, twist or align vertebrae V to a selected orientation for sagittal, coronal and/or axial correction.

Figure 10:
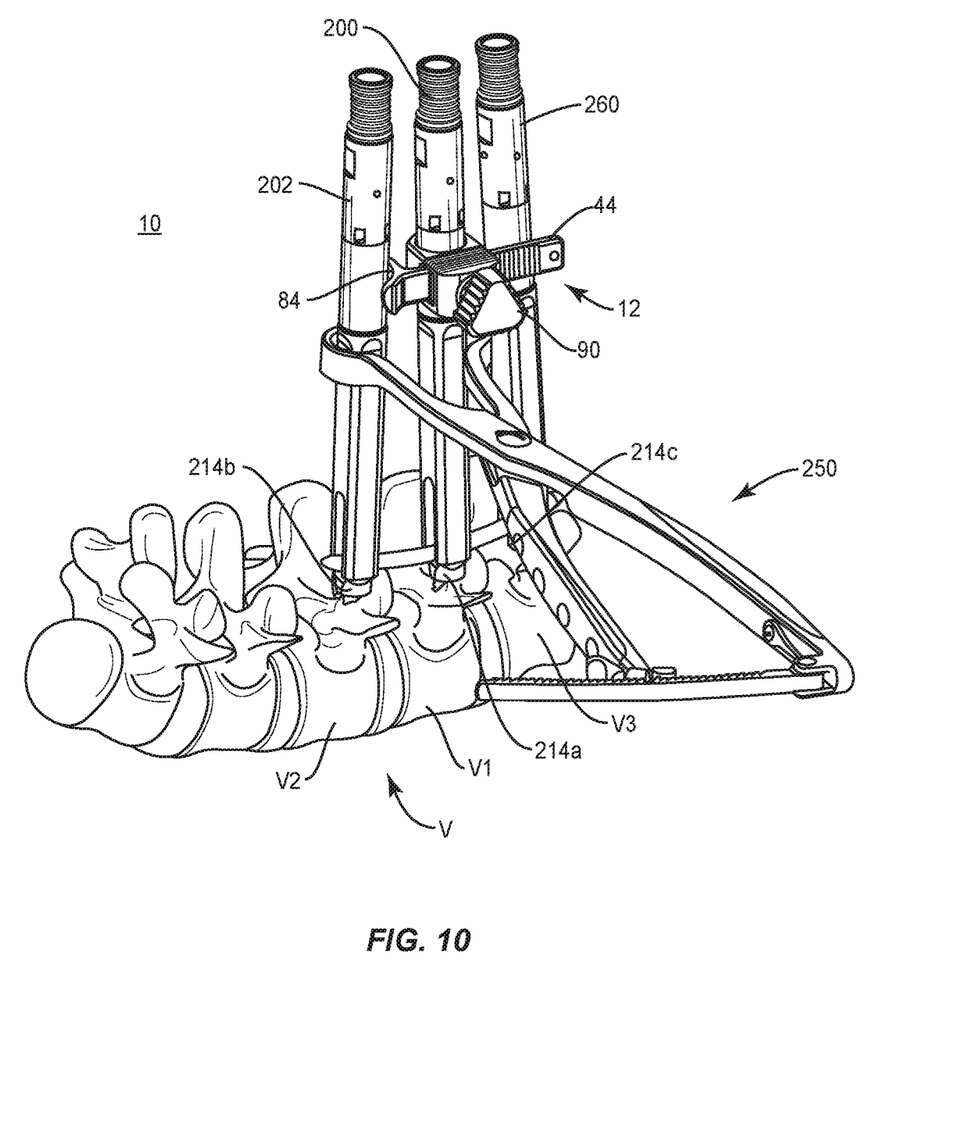
FIG. 10 is a perspective view of components of one embodiment of a surgical system in accordance with the principles of the present disclosure disposed with vertebrae.
Figure 11:
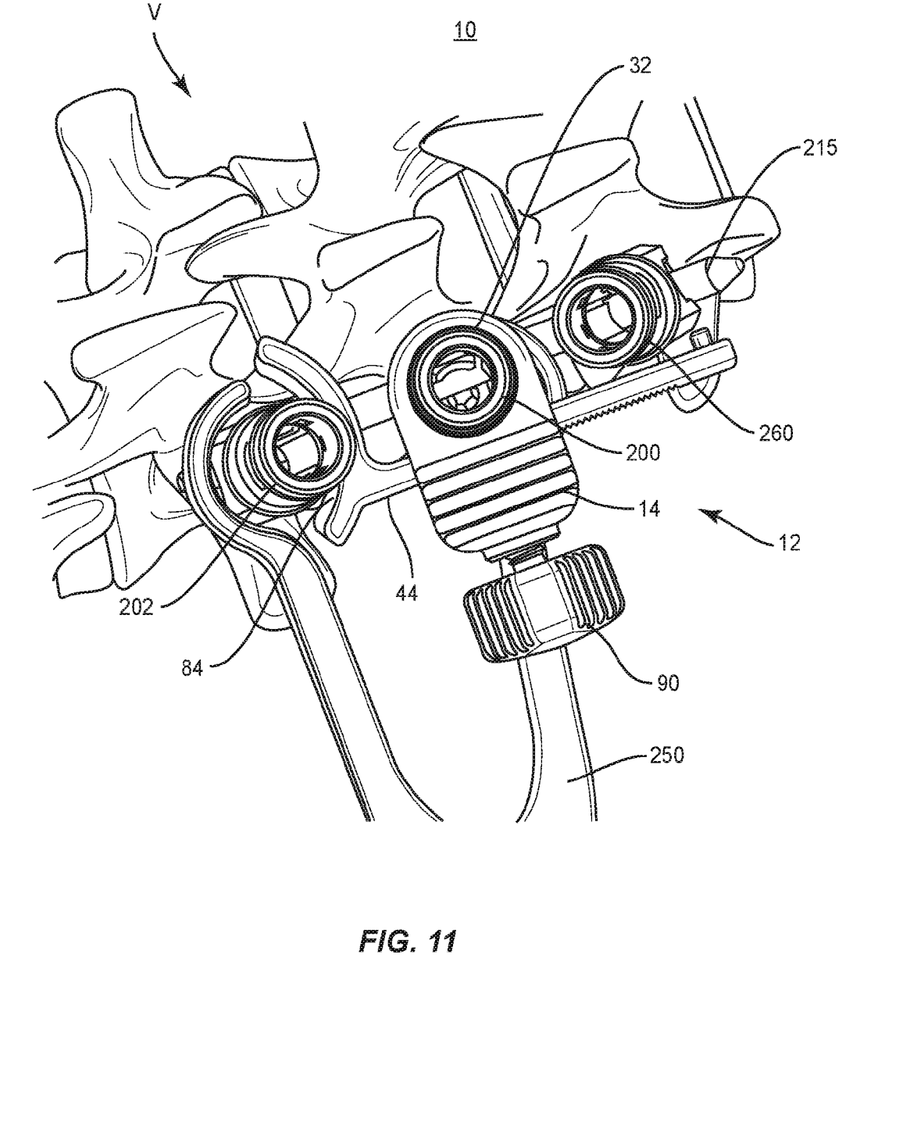
FIG. 11 is a perspective view of components of one embodiment of a surgical system in accordance with the principles of the present disclosure disposed with vertebrae.

In some embodiments, as shown in FIGS. 10 and 11, fulcrum 12 is configured to facilitate clearance for an adjacent implant support, such as, for example, an extender 260. Extender 260 is disposed with a bone fastener 214c and an adjacent portion of spinal rod 215. Extenders 200, 202, 206 are oriented for alignment with spinal rod 215 and an axis thereof. Fulcrum 12 is disposed in fixed position and locking orientation with extenders 200, 202, as described with regard to FIGS. 7-9. Slide 44 is disposed with body 14 and extends axially and in substantially parallel orientation with the axis of spinal rod 215. Slide 44 is offset from the axis of spinal rod 215 to provide clearance for and adjacent to extender 206.

In some embodiments, use of microsurgical and image guided technologies may be employed to access, view and repair spinal deterioration or damage, with the aid of spinal correction system 10. Upon completion of the procedure, the non-implanted components, surgical instruments and assemblies of spinal correction system 10 are removed and the incision is closed.

In some embodiments, spinal correction system 10 comprises a kit including a plurality of interbody devices, plates, bone fasteners and/or fixation elements, which may be employed with a single vertebral level or a plurality of vertebral levels. In some embodiments, the fasteners may be engaged with vertebrae in various orientations, such as, for example, series, parallel, offset, staggered and/or alternate vertebral levels. In some embodiments, the fasteners may be configured as multi-axial screws, sagittal angulation screws, pedicle screws, mono-axial screws, uni-planar screws, fixed screws, anchors, tissue penetrating screws, conventional screws and expanding screws. In some embodiments, the fasteners may be employed with wedges, anchors, buttons, clips, snaps, friction fittings, compressive fittings, expanding rivets, staples, nails, adhesives, posts, connectors, fixation plates and/or posts. In some embodiments, spinal correction system 10 includes surgical instruments, such as, for example, inserters, extenders, reducers, spreaders, distracters, blades, retractors, clamps, forceps, elevators and drills, which may be alternately sized and dimensioned, and arranged as a kit.

In some embodiments, spinal correction system 10 includes an agent, which may be disposed, packed, coated or layered within, on, adjacent or about the components and/or surfaces of spinal correction system 10, and/or disposed with tissue. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a fulcrum extending along an axis between opposite top and bottom walls, the fulcrum including opposite first and second side walls each extending from the top wall to the bottom wall, the fulcrum comprising opposite first and second end walls each extending from the top wall to the bottom wall and from the first side wall to the second side wall, the top and bottom walls defining a cavity extending parallel to the axis and configured for disposal of a first implant support, the fulcrum comprising a passageway extending perpendicular to the axis through the side walls, the first end wall defining a window, the window being in communication with the passageway and the cavity; and
   a slide having a first end positioned in the passageway and an opposite second end, the slide being movable relative to the fulcrum and engageable with the first implant support to fix the first implant support with the fulcrum, the second end being engageable with a second implant support.

2. A surgical instrument as recited in claim 1, further comprising a screw extending through an aperture in the first end wall such that an end of the screw is engageable with the slide within the passageway.

3. A surgical instrument as recited in claim 1, wherein the first end is slidably engageable with the first implant support.

4. A surgical instrument as recited in claim 1, wherein the first end comprises an arm defining a second axis, the second end comprising a leg extending transverse to the second axis.

5. A surgical instrument as recited in claim 4, wherein the leg comprises a concave surface.

6. A surgical instrument as recited in claim 1, wherein the first end comprises an arm, the arm being disposable with the fulcrum between a non-locking orientation such that the arm is translatable relative to the fulcrum and a locked orientation such that the arm is fixed in position with the fulcrum.

7. A surgical instrument as recited in claim 1, wherein the fulcrum includes a part that biases the slide into engagement with the first implant support.

8. A surgical instrument as recited in claim 7, wherein the part resiliently biases the slide into engagement with the first implant support.

9. A surgical instrument as recited in claim 7, wherein the part is engageable with the slide in a non-locking orientation such that the first implant support is movable through the cavity and relative to the fulcrum, and a locked orientation such that the first implant support is fixed in position with the fulcrum.

10. A surgical instrument as recited in claim 1, further comprising a lock that fixes the slide in position with the fulcrum when the lock is in a locked orientation.

11. A surgical instrument as recited in claim 10, wherein the lock includes a screw connected with a clamp that engages the slide to fix the slide in position with the fulcrum when the lock is in the locked orientation.

12. A surgical instrument as recited in claim 11, wherein the screw is fixed with and rotatable relative to the clamp.

13. A surgical instrument as recited in claim 1, wherein the slide is disposable in a non-locking orientation such that the slide and the first implant support are provisionally fixed in position relative to the fulcrum and a locking orientation such that the slide and the first implant support are locked in position relative to the fulcrum.

14. A surgical instrument as recited in claim 1, wherein the fulcrum is fixed with the first implant support via a friction fit engagement.

15. A surgical instrument as recited in claim 1, wherein the first end comprises an arm, the arm comprising a plurality of teeth disposed in a linear orientation.

16. A surgical instrument as recited in claim 15, further comprising a lock disposed in the passageway, the lock being movable relative to the fulcrum and having teeth engageable with the teeth of the arm to fix the slide in position with the fulcrum.

17. A surgical instrument as recited in claim 1, wherein the cavity has a circular cross-sectional configuration.

18. A surgical instrument comprising:
   a fulcrum extending along an axis between opposite top and bottom walls, the fulcrum including opposite first and second side walls each extending from the top wall to the bottom wall, the fulcrum including first and second end walls each extending from the top wall to the bottom wall and from the first side wall to the second side wall, the top and bottom walls defining a cavity extending parallel to the axis and configured for disposal of a first implant support, the fulcrum comprising a passageway extending perpendicular to the axis through the side walls, the first end wall defining a window, the window being in communication with the passageway and the cavity;

an arm positioned in the passageway and biased to engage the first implant support and fix the fulcrum with the first implant support, the arm being translatable relative to the first implant support and engageable with a second implant support; and a lock extending through the first end wall to fix the arm in position with the fulcrum.

19. A surgical instrument comprising:

a fulcrum extending along an axis between opposite top and bottom walls, the fulcrum including opposite first and second side walls each extending from the top wall to the bottom wall, the fulcrum including first and second end walls each extending from the top wall to the bottom wall and from the first side wall to the second side wall, the top and bottom walls defining a cavity extending parallel to the axis and configured for disposal of a first implant support, the fulcrum comprising a passageway extending perpendicular to the axis through the side walls, the first end wall defining a window, the window being in communication with the passageway and the cavity;

an arm positioned in the passageway and biased to engage the first implant support and fix the fulcrum with the first implant support, the arm being translatable relative to the first implant support and engageable with a second implant support; and a screw extending through the first end wall and engageable with the arm to fix the arm in position with the fulcrum.

20. A surgical instrument as recited in claim 19, wherein the first end wall comprises spaced apart first and second blind holes, the surgical instrument comprising a first spring positioned in the first blind hole and a second spring positioned in the second blind hole, the springs each directly engaging a pressure plate within the passageway, the pressure plate having an opening, a clamp plate being positioned in the opening of the pressure plate, the clamp plate comprising teeth configured to engage teeth of the arm to fix the arm relative to the fulcrum.

* * * * *